(12) United States Patent
Nicoletti

(10) Patent No.: US 8,304,442 B2
(45) Date of Patent: Nov. 6, 2012

(54) COMPOUNDS HAVING IMMUNOMODULATOR ACTIVITY

(75) Inventor: Ferdinando Nicoletti, Cannizzaro (IT)

(73) Assignee: Ganial Immunotherapeutics, Inc., Locust Valley, NY (US)

( * ) Notice: Subject to any disclaimer, the term of this patent is extended or adjusted under 35 U.S.C. 154(b) by 465 days.

(21) Appl. No.: 11/908,472

(22) PCT Filed: Mar. 14, 2006

(86) PCT No.: PCT/EP2006/002319
§ 371 (c)(1), (2), (4) Date: Apr. 30, 2008

(87) PCT Pub. No.: WO2006/097273
PCT Pub. Date: Sep. 21, 2006

(65) Prior Publication Data
US 2009/0042959 A1  Feb. 12, 2009

Related U.S. Application Data

(60) Provisional application No. 60/661,500, filed on Mar. 15, 2005.

(51) Int. Cl.
*A61K 31/42* (2006.01)
*A01N 43/80* (2006.01)
*C07D 261/02* (2006.01)

(52) U.S. Cl. ........................ 514/378; 548/240

(58) Field of Classification Search .............. 514/378; 548/340
See application file for complete search history.

(56) References Cited

U.S. PATENT DOCUMENTS
5,716,967 A  2/1998  Kleinman
5,849,736 A  12/1998  Wityak et al.
6,114,367 A  9/2000  Cohan et al.

FOREIGN PATENT DOCUMENTS
WO  02/100332 A2  12/2002

OTHER PUBLICATIONS

Onodera, Induction of cyclooxygenase-1 in cultured synovial cells isolated from rheumatoid arthritis patients, Inflamm. res. 53, 217-222, 2004.*
Alegre, Cellular mechanisms underlying acute graft rejection: time for reassessment, Current Opinion in Immunology 2007, vol. 19, pp. 563-568, See conclusion.*
Mocellin, Interleukin-10 and the immune response against cancer: a counterpoint, Journal of Leukocyte Biology vol. 78, Nov. 2005.*
Enfer, Sam, Inflammation 2005—Seventh World Congress. Highlights II, The Investigational Drugs Journal, Oct. 2005; 8(10):791-792.
Durez, P., et al., In Vivo Induction of Interleukin 10 by Anti-CD3 Monoclonal Antibody or Bacterial Lipopolysacchardide: Differential Modulation by Cyclosporin A., J. Exp. Med., Feb. 1993; 17:551-555.

Vicari, A. P., et al., Interleukin-10 in viral diseases and cancer: exiting the labyrinth?, Immunological Reviews, 2004; 202:223-236.
Eichinger, K., et al., A Convenient Synthesis of 3- and 3,4-Substituted 4,5-Dihydroisoxazole-5-Acetic Acids, Synthetic Communications, Aug. 1997; 27(16):2733-2742.
Muti, G., et al., Epstein-Barr Virus (EBV) Load and Interleukin-10 in EBV-positive and EBV-negative post-transplant Lymphoproliferative Disorders, British Journal of Haematology, Sep. 2003; 122(6):927-933.
Eichinger, K., et al., A Novel Base Promoted Reaction of Methyl 2-Isoxazoline-5-acetates to 5-(2-oxoethyl)-3-isoxazolidinones, Synthetic Communications, Jul. 1998; 28(13):2457-2466.
Kaneko, T., et al., Proinflammatory effects of exogenously administered IL-10 in experimental autoimmune orchitis, Cytokine, Apr. 2003; 22(1-2):50-53.
Rosenbaum, J. T., et al., Paradoxical effects of IL-10 in endotoxin-induced uveitis, Journal of Immunology, Oct. 1995; 155(8):4090-4094.
Li, M., et al., IL-10 and it's related cytokins for treatment of inflammatory bowel disease, World Journal of Gastroenterology, 2004; 10:620-625.

(Continued)

*Primary Examiner* — Benjamin Packard
*Assistant Examiner* — Adam C Milligan
(74) *Attorney, Agent, or Firm* — Thomas Kim

(57) ABSTRACT

Compounds of formula I

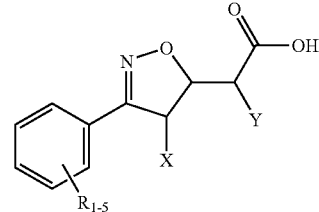

wherein I, $R_{1-5}$ represents from one to five substituents independently selected from hydrogen, nitro, cyano, $C_1$-$C_3$-alkyl, halogen, carboxy, amino, trifluoromethyl, hydroxy, $C_1$-$C_3$-alkoxy groups, X is hydrogen, halo, $N_3$, SH, =O, =$CH_2$, an aromatic, preferably phenyl, ring optionally substituted by $R_{1-5}$ groups as defined above, amino, mono- or disubstituted amino groups wherein the substituents are selected from $C_1$-$C_4$ alkyl, phenyl or benzyl groups optionally substituted by $R_{1-5}$ groups as defined above Y is hydrogen, alkyl $C_1$-$C_4$, amino, or a group of formula —$(CH_2)_{0-1}$A wherein A is an aromatic, preferably phenyl, ring optionally substituted by $R_{1-5}$ groups as defined above with the proviso that when X and Y are hydrogen, $R_{1-5}$ cannot represent a 4-hydroxy or 4-alkoxy groups, are useful for the treatment of Tumor Necrosis Factor mediated immunopathological conditions as well as of diseases which may be treated or alleviated by inhibition of Interleukin-10 (IL-10).

6 Claims, No Drawings

OTHER PUBLICATIONS

Trabattoni, D., et al., B7-H1 is up-regulated in HIV infection and is a novel surrogate marker of disease progression, Blood, Apr. 1, 2003; 101(7):2514-2520.

Llorente, L., et al., Clinical and Biologic Effects of Anti-Interleukin-10 Monoclonal Antibody Administration in Systemic Lupus Erythematosus, Arthritis & Rheumatism, Aug. 2000; 43(8):1790-1800.

Balasa, B., et al., Islet-Specific Expression of IL-10 Promotes Diabetes in Nonobese Diabetic Mice Independent of Fas, Perforin, TNF Receptor-1, and TNF Receptor-2 Molecules, Journal of Immunology, 2000; 165:2841-2849.

* cited by examiner

COMPOUNDS HAVING IMMUNOMODULATOR ACTIVITY

CROSS-REFERENCE TO RELATED APPLICATIONS

This application is a national stage application of PCT International Application PCT/EP2006/002319, filed Mar. 14, 2006, which claims priority to U.S. Provisional Patent Application 60/661,500, filed Mar. 15, 2005.

The present invention refers to the use of compounds for the treatment of autoimmune diseases, chronic inflammations, immune-mediated diseases, pathological conditions mediated by cytokines that include but are not limited to Tumor Necrosis Factor (TNF) alpha, interleukin (IL) 1 beta, IL-10 associated or not to hyper activation of NFkB and pathological conditions which may be treated or alleviated by the inhibition of cytokines that include but are not limited to TNF-alpha, TNF-beta, IL-1beta and IL-10 and/or of NFkB activation.

BACKGROUND OF THE INVENTION

The better understanding of immunopathogenic pathways involved in the onset of autoimmune diseases, chronic inflammations or other immune-mediated diseases, have allowed to identify the key rote played in T-cell mediated autoimmune diseases by cytokines such as TNF-alpha, TNF-beta, IL-1beta, IL-12, IL-18 and IFN-gamma. In particular, the experimental evidences anticipating a key pathogenetic role of TNF-alpha in the pathogenesis of rheumatoid arthritis have been successfully translated to the clinical stage as specific inhibitors, namely a neutralizing monoclonal antibody [Infliximab, Humana] and a TNF receptor fusion protein, [Embrel] are currently approved for the treatment of RA patients.

Double blind clinical studies have proven that the neutralization of TNF can completely abrogate the early stage of inflammation. The specific inhibitors of TNF-alpha, in contrast to acetylsalicylic acid that subsides the inflammation, can prevent the inflammation. At first, the treatment was administered to patients with advanced disease. Upon the great beneficial success of the medication, physicians began to treat patients at an early stage of the disease. Treatment with the anti-TNF alpha drug is now utilized in other autoimmune diseases, including Crohn's disease and psoriasis. However, the production of the specific TNF-inhibitors is complex and expensive. Moreover, anti-TNF inhibitors can be only given parenterally and their chronic use may involve a greater risk of developing tuberculosis.

The demonstration of the beneficial effects of specific TNF-inhibitors in rheumatoid arthritis, Crohn's disease and psoriasis has generated efforts to discover orally available small compounds that inhibit the synthesis and/or the action of endogenous TNF and possibly other cytokines that include IFN-gamma, IL-1, IL-12, IL-18 or other cytokines.

Autoimmune diseases are immunomediated diseases that can be defined according to the organ that is attacked, according the attacking mechanism, is mediated by autoantibody or T-cells, and the development of chronic inflammation processes often mediated by cytokines. Increasing evidences suggests an important pathogenic contribution of autoimmune phenomena to atherosclerosis, psychiatric disease schizophrenia, epilepsy, baldness, peptic ulcer disease, and others.

Autoimmune diseases can affect every organ or tissue. There are autoimmune diseases that affect the nervous system, for example, multiple sclerosis. This severe disease damages the brain and causes paralysis. Other autoimmune diseases that affect the nervous system are myasthenia gravis and Guillain-Barré syndrome. Myasthenia gravis is a disease characterized by extreme muscle weakness in which the receptor that transmits electric impulse from the nerve to the muscle is destroyed. Without the transmission, there is no muscle contraction and therefore muscle weakness develops. Guillain-Barré syndrome may develop after an infection or vaccination.

There are autoimmune diseases that affect the joints, such as lupus and rheumatoid arthritis that causes deformities to the Joints. Finally, there are autoimmune diseases that damage the heart, kidneys, and lungs.

DESCRIPTION OF THE INVENTION

Isoxazoline compounds have been disclosed as inhibitors of phosphodiesterase type IV (U.S. Pat. No. 5,716,967), fibrinogen receptor antagonists (U.S. Pat. No. 5,849,736), inhibitors of TNF release (U.S. Pat. No. 6,114,367) and as macrophage migration inhibitory factor (MIF) antagonists (WO 02/100332).

It has now been found that compounds of formula I, differing from those disclosed in U.S. Pat. No. 5,716,967, U.S. Pat. No. 5,849,736, and WO 02/100332 in the absence of an hydroxyl or alkoxy group in the para position of the phenyl ring, inhibits IL-1β, TNF-α and IL-10 synthesis and prevents NFkB activation.

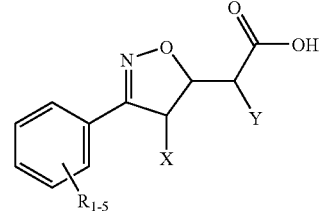

In formula I, $R_{1-5}$ represents from one to five substituents independently selected from hydrogen, nitro, cyano, $C_1$-$C_3$-alkyl, halogen, carboxy, amino, trifluoromethyl, hydroxy, $C_1$-$C_3$-alkoxy groups, X is hydrogen, halo, $N_3$, SH, =O, =$CH_2$, an aromatic, preferably phenyl, ring optionally substituted by $R_{1-5}$ groups as defined above, amino, mono- or disubstituted amino groups wherein the substituents are selected from $C_1$-$C_4$ alkyl, phenyl or benzyl groups optionally substituted by $R_{1-5}$ groups as defined above Y is hydrogen, allyl $C_1$-$C_4$, amino, or a group of formula —$(CH_2)_{0-1}$A wherein A is an aromatic, preferably phenyl, ring optionally substituted by $R_{1-5}$ groups as defined above with the proviso that when X and Y are hydrogen, $R_{1-5}$ cannot represent a 4-hydroxy or 4-alkoxy groups.

Some of the compounds of formula I are known or can be prepared by known methods. The compound wherein R and R' are both hydrogen and a 4,5-dihydro isoxazoline ring system have been reported by Synth. Comm., 1998, 28(13), 2457-2466 and from Synth. Comm., 1997, 27(16), 2733-2742.

The invention described in this document concerns therefore the use of compounds of formula I for the preparation of a medicament for the treatment of those diseases which may be alleviated by the inhibition of TNF alpha, TNF-beta, IL-1beta and/or IL-10 associated or not to dysregulated activation NFkB. Preferred compounds of formula I are 3-phenyl-4,5-dihydro-5-isoxazoleacetic acid (hereinafter referred to as GIT27) and 3-phenyl-5-isoxazoleacetic acid as well as their pharmaceutically acceptable salts, such as sodium, potassium, calcium salts and the like. GIT27 is particularly preferred.

The compounds of the invention are particularly useful for the treatment of human pathologies mediated by TNF alpha, TNF-beta, IL-1beta and/or IL-10 associated or not to an activation of NFkB. Said pathologies include immuno-inflammatory, autoimmune and infectious diseases including rheumatoid arthritis, Crohn's disease, psoriasis and inflammatory dermatoses, type 1 diabetes, HIV infections, cancer, ischemia-reperfusion, hepatitis, multiple sclerosis, Guillain-Barré syndrome and prevention of acute graft rejection.

The invention therefore also concerns pharmaceutical compositions comprising a compound of formula I as the active ingredient in admixture with a suitable carrier or excipients.

DETAILED DESCRIPTION OF THE INVENTION

The pharmacological activity of GIT-27 has been extensively studied both in vitro and in vivo. More particularly, the following experiments have been carried out, according to known and well-established methods:
lymphoproliferation, TNF-alpha, Interferon (IFN)-gamma, IL-1 beta, IL-10 and MIF synthesis/secretion;
NF-kB activation in human macrophages;
murine LPS-induced lethality;
murine Carrageenan-induced pleurisy;
murine type II collagen-induced arthritis;
murine oxazolone-induced hypersensitivity;
murine immunoinflammatory diabetes induced by multiple low doses of streptozotocin;
chemically-induced colitis in mice;

The results obtained performing the experiments listed above are hereinafter summarized.

In Vitro Effect of GIT27 on Proliferation of Lymphocytes and on TNF, IFN-gamma, IL-10 and MIF Synthesis and Secretion by Macrophage and Lymphocyte Peritoneal macrophages (PM) and splenic mononuclear cells (SMNC) were isolated from normal mice, were cultured in nutrient medium and stimulated with LPS and/or ConA, respectively in the absence or presence of GIT27. The results clearly show that GIT27 markedly inhibited the production of TNF α by both PM and SMNC and inhibited the production of IL-1β IL-10 by PM. GIT27 had no effect on MIF expression in either cell type, on proliferation of SMNC, and on IL-10 and Interferon (IFN) gamma production by SMNC.

Proliferative and cytokine synthesis capacity of lymphocytes and macrophages isolated from GIT27 treated mice.

These experiments were carried out to explore if intraperitoneal (i.p.) or per os (p.o.) treatment of mice with GIT27 could influence the proliferative response of SMNC and the production of IL-1β, IL-10, TNF-α, IFN-γ and MIF from isolated PM and SMNC. PM and SMNC isolated from mice treated in vivo with GIT27 for 7 consecutive days i.p. (0.5 mg/mouse), or p.o. (2.5 mg/mouse), or isolated from control animals that received GIT27 vehicle ($Na_2HPO_4/H_2O$), or were without any treatment. 24 h after the last GIT27 treatment, PM and SMNC were collected for further in vitro stimulation and analysis.

This ex vivo experiment clearly shows that PM's isolated from GIT27 treated mice exhibit impaired synthesis of IL-1β, TNF α and IL-10 while showing a normal pattern of MIF expression upon mitogenic stimulation. On the other hand, the SMNC isolated from GIT27 treated mice show a normal capacity to proliferate, a normal capacity to produce TNF-α, IL-1β, IL-10, and IFN-γ upon stimulation, and a normal expression pattern of MIF expression.

The findings from "in vitro" and "ex vivo" experiments concordantly show that GIT27 down-regulates the production of IL-1β, TNF-α and IL-10 by PM without altering the capacity of SMNC to produce IFN-γ and does not affect the expression of MIF by PM and SMNC. In contrast the "in vitro" experiments show that GIT27 reduced TNF-α production by SMNC while the "ex vivo" experiments do not support this evidence.

Effect of GIT27 on NF-kB Activation in Human Macrophages

The results from this in vitro test indicate that GIT27 powerfully inhibits in a dose-dependent fashion the DNA binding of NF-kB that LPS induced in monocyte-derived human macrophages. These results provide evidence for the mechanism of action of GIT27 and suggest that the inhibitory effects that GIT27 exerts on macrophage synthesis of IL-1β, TNF-α and IL-10 might secondary to the inhibition of NF-kB binding to DNA.

Effect of GIT27 on LPS-Induced Lethality In Vivo

This in vivo study showed that the therapeutic administration of GIT27 powerfully counteracts LPS-induced lethality in mice.

As expected, most of the control mice either untreated or that received the vehicle of GIT27 succumbed to LPS-challenge within 3 days. After this period of observation, one-week follow-up of the surviving mice revealed a full clinical recovery. In contrast, the treatment with GIT27 given either po or ip protect the mice from the lethal effects of LPS in a dose-dependent fashion. When given p.o., GIT27 was effective at the dose of 2.5 mg/mouse and dosed out both at 1.5 and 3 mg/mouse. When given i.p., GIT27 exhibited a wider therapeutic window with dose-dependent protection against LPS-induced lethality between 0.25 and 0.5 mg/mouse. GIT27 was also capable of significantly reducing LPS-induced lethality when it was given both p.o. and i.p. at similar doses under a prophylactic regime (e.g. -24 and -1 hour prior to LPS).

Effect of GIT27 on Carrageenan (CAR) Induced Pleurisy

GIT27 powerfully suppresses CAR-induced pleurisy in mice All the mice that were challenged with CAR and left untreated or treated with the vehicle of GIT27 developed an acute pleurisy, with production of turbid exudate, PMNs infiltration, and myeloperoxidase (MPO) activity accumulation in the lung. In contrast the prophylactic treatment with GIT27 reduced the production of exudate, the PMNs infiltration, and mycloperoxidase (MPO) activity accumulation in the lung and exerted a powerful protective effect that was comparable to that achieved with the treatment with antibody against mouse TNF-alpha that was used as positive control drug.

Effect of GIT27 on Type II Collagen-Induced Arthritis (CIA)

To evaluate the therapeutic effect of GIT27 in arthritis, mice developing type II CIA were treated for 10 consecutive days. The treatment started when the mice showed a clinical score≧1. Control mice were treated under the same experimental regime with the vehicle of GIT27.

The vehicle-treated control mice rapidly develop full clinical signs of type II CIA with a progressive increment of the arthritic clinical scores and severe hind paws oedema. This clinical picture was reflected by severe inflammatory arthritis as indicated by the high the progressive increment of the arthritic histological scores determinated by histological evaluation. In contrast, GIT27-treated mice exhibited a significantly slower progression of the arthritic disease with lower clinical and histological arthritic scores than the vehicle-treated mice. The therapeutic treatment with GIT27 produced a marked anti-inflammatory effects on murine type II CIA, leading to significant reduction of both clinical and histological parameters associated to development of the disease. The therapeutic potency of GIT27 was comparable to that of the positive control drug dexamethasone.

Effect of GIT27 on Oxazolone-Induced Dermatitis

Oxazolone-induced hypersensitivity is an immune-mediated dermatitis that can be induced by two epicutaneous exposure to oxazolone. While the first application of oxazolone sensitizes the mice, the second elicits the hypersensitivity reaction. The dermatitis manifestations appear 18 hours after the second epicutaneous exposure to oxazolone, both ear thickness and weight markedly and progressively increase. The in vivo studies to assess the pharmacological activity of GIT27, were planned with two set of experimental. In the first set, the mice were treated during or before the sensitization phase. This experiment shows that ear thickness and weight markedly and progressively increased in the mice that had been treated with either the vehicle of GIT27 or were left untreated. In contrast, the inflammatory swelling of the ear, as measured by the increment of ear thickness and weight, was significantly suppressed by GIT27. In similar conditions, dexamethasone reduced the thickness but not the weight of the ears.

To evaluate the effects of GIT27 on the elicitation phase of oxazolone-induced dermatitis, the treatment with GIT27 was given one hour after the second epicutaneous exposure to oxazolone, when start the progression of the immunoinflammatory responses. Under this experimental regime, GIT27 only partially affected the development of allergic dermatitis. In comparison with control animals, the mice, treated with GIT27 only exhibited a significant decrease of the thickness but not of the weight of the ears. In this experimental regime, dexamethasone did not affect the increase of ear thickness and weight.

The result of this experiment shows that treatment with GIT27 can successfully suppress the dermatitis induced by repeated epicutaneous exposure to oxazolone when GIT27 was administered upon profilactic regime, that is prior to the sensitisation phase of the disease.

However, GIT27 is less potent in preventing or blocking the development of oxazolone-induced dermatitis if it was administered to the mice one hour after the second exposure to oxazolone (elicitacion phase). Nonetheless, this effect acquires pharmacological relevance in light of the lack of effects of dexamethasone when given under the same experimental regime. Since dexamethasone is a powerful immunosuppressant widly and effectively used for the topical treatment of human inflammatory skin diseases, GIT27 shows pharmacological potentials for the systemic or topical use in the treatment of immune-mediated or type 1 cytokine dependent skin diseases such as psoriasis, some forms of pemphigus vulgaris and cutaneous vasculitis during graft versus host disease.

Effect of GIT27 on Streptozotocin Induced Diabetes

Both i.p and p.o. treatment with GIT27 suppressed clinical development of diabetes that is induced in CBA/H mice by multiple low doses of streptozotocin. CBA/H mice developed sustained hyperglycaemia over a 2-week period following MLD-STZ injections. As expected, CBA/H control mice treated with the vehicle of GIT27 either i.p. or p.o. develop diabetes with sustained hyperglycaemia developed over a 2-week period following MLD-STZ injections. In contrast, the diabetogenic effect of MLD-STZ was significantly reduced when the mice were treated with GIT27 i.p. The drug was also capable of significantly reducing development of hyperglycaemia when administered p.o.

The prophylactic treatment with GIT27 given either i.p. and p.o., successfully counteracted the development of hyperglycaemia that is secondary to the cell-mediated immune destruction of the beta cells after consecutive injections of STZ. The drug was effective both when given i.p. and p.o. These results suggest that GIT27 possesses pharmacological properties worthy of being further considered for clinical use in the early treatment of human type 1 diabetes (T1D) as well as in the prevention of the disease in individuals at risk for its development such as those first degree relatives of patients with T1D that exhibit metabolic (defective insulin secretion) and immunologic parameters (anti-beta cell autoantibodies, HLA haplotypes) associated with high risk of T1D development.

Effect of GIT27 on DNB-Induced Colitis

Within 5 days after challenge with dinitrobenzene sulfonic acid (DNB), mice develop colitis. The disease severity is evaluated based on a macroscopic score. The vehicle-treated control mice and untreated mice developed colitis with a predictable and progressive increase in inflammation and body weight loss. The progression of inflammatory colitis was significantly attenuated in those animals, which had been treated with GIT27 ($p<0.001$). In comparison with the control groups, the GIT27 treated animals show a significant reduction in weight loss. In agreement with these data, the increase in colon weight that accompanies the development of DNB-induced colitis was significantly lower in the mice treated with GIT27 as compared to the controls.

The colons of the control mice and of the GIT27 treated mice were removed, sectioned, fixed, and stained with hematoxylin and eosin. A reduction in the inflammatory cellular infiltrate, mucosal and muscle damage, as well as wall thickening were observed in the animals that were treated with GIT27 before DNB-induced colitis. The histology clearly indicates that the tissue damage is significantly reduced in the mice treated with GIT27 as compared to the control mice. These data confirm the anti-inflammatory efficacy of GIT27 in colitis. The tissue myeloperoxidase activity is a well established marker to assess the inflammatory cell (mainly neutrophils) infiltration. The myeloperoxidase activity measured in the colon tissues collected from GIT27 treated mice and from control mice clearly indicate that the mice treated with GIT27 show a significant reduction of inflammatory cell infiltration 5 days after the induction of colitis as compared to controls ($p<0.0001$). This result parallels the reduction of neutrophils infiltrating the same histology samples. We counted an average of $8,9\pm1.2$ (means$\pm$SD) cells/high power field in the of DNB-induced animals, whereas there were only $3.37\pm0.8$ cells/high-power field in DNB-induced animals pretreated with GIT27 ($p<0.0001$). These data prove that the treatment with GIT27 powerfully protect the test animals from the colitis that is induced by the administration of DNB. The present data indicate that this drug hold promises for its possible use in the treatment of human IBD.

Effect of GIT27 on Immune-Mediated Diseases Such as Autoimmune Diseases and Chronic Inflammations The in vitro and in vivo results obtained using GIT27, show that this molecule has the pharmacological potential to be an interesting drug for the treatment of those diseases that are mediated by immune mechanisms such as autoimmune diseases and chronic inflammations, and some skin diseases and endocrinediseases. In general GIT27 has a potential in the therapy of those diseases that are mediated by IL-1β, TNF or other cytokines.

Because IL-10 anti-inflammatory properties (World J. Gastroenterol., 10; 620, 2004), the inhibitory effect that GIT27 exert on the macrophage synthesis of this cytokine may appear not consistent with the use of this drug in immunoinflammatory diseases. Nonetheless, IL-10 has also been shown to exert proinflammatory effects in different rodent models such as endotoxin induced uveitis (J. Immunol., 1995, 155: 4090-4), type 1 diabetes (J. Immunol. 2000, 165:2841-9), systemic lupus erythematosus (Arthritis Rheum. 2000, 43:1790-800.) and experimental autoimmune orchitis (Cytokine. 2003, 22:50-3.). It is therefore possible that under certain circumstances the reduction of IL-10 synthesis may actually enhance the anti-inflammatory efficacy of a drug. This is also consistent with the fact that Cyclosporin A that is widely used in the clinical setting for the treatment of autoimmune diseases also down-regulates IL-10 synthesis in vitro (J. Exp Med. 199317:551-5). In addition, since exuberant production of IL-10 has been thought to play a pathogenic role in certain cancers (Immunol Rev. 2004 December; 202: 223-36.; Br J Haematol. 2003, 122:927-33) and HIV infections (Blood. 2003, 101:2514-20.), the capacity of GIT27 to down-regulate the synthesis of this cytokine represents a potential rationale for the potential investigation of this drug in these diseases.

For the considered therapeutic uses, the compounds of formula I will be administered by the oral, parenteral, transdermal or transmucosal routes in form of suitable compositions in admixture with conventional carrier or excipients, prepared according to known methods. The dosage will depend on several factors, such as the seriousness of the pathology, the kind of patient (age, sex and weight) and will be anyhow easily determined by the skilled practitioner on the basis of the toxicological and pharmacokinetic properties of the drug.

Preparation of GIT27

Benzaldehyde (1, 32.8 mmol) and hydroxylamine hydrochloride (33 mmol) were dissolved in methanol (100 ml) followed by addition of sodium carbonate (65 mmol). Overnight reaction gave the oxime derivative in 95% (2, 30.4 mmol). Chlorination of the oxime using N-chlorosuccinimide (31.6 mmol) in DMF (100 ml) quantitatively furnished chlorooxime (3). Compound 3 was then dissolved in THF/H2O (*0/20) and treated with 3-butenoate (24.5 mmol) and sodium carbonate (73.6 mmol). After completion, (12 h), the product was extracted with ethyl acetate and the organic extracts were washed with brine and dried over magnesium sulfate. GIT-27 was crystallized from ethyl acetate/heptane mixture. The structure was confirmed by 1H-NMR, 13C-NMR and mass spectroscopy. The daily dosage regimen will presumably vary within wide ranges, for instance from 0.1 to 10 mg/kg body weight.

The invention claimed is:

1. A method for the treatment of immunopathological conditions that are either mediated by tumor necrosis factor or result from diseases which may be treated or alleviated by inhibition of Interleukin-10 in a subject in need thereof, comprising administering to said subject a pharmaceutical composition comprising a compound selected from 3-phenyl-4,5-dihydro-5-isoxazoleacetic acid, 3-phenyl-5-isoxazoleacetic acid and pharmaceutically acceptable salts thereof.

2. The method of claim 1, wherein the compound is 3-phenyl-4,5-dihydro-5-isoxazoleacetic acid or pharmaceutically acceptable salt thereof.

3. The method of claim 1, wherein the disease is selected from the group consisting of immuno-inflammatory, autoimmune and infectious diseases in humans.

4. The method of claim 2, wherein the diseases are selected from the group consisting of immuno-inflammatory, autoimmune and infectious diseases in humans.

5. The method of claim 1, wherein the disease is rheumatoid arthritis.

6. The method of claim 2, wherein the disease is rheumatoid arthritis.

* * * * *